United States Patent [19]

Faisandier

[11] Patent Number: 5,800,473
[45] Date of Patent: Sep. 1, 1998

[54] SYSTEMS, METHODS, AND APPARATUS FOR AUTOMATIC UPDATING OF A PROGRAMMER FOR AN ACTIVE IMPLANTABLE MEDICAL DEVICE

[75] Inventor: Yves Faisandier, Paris, France

[73] Assignee: ELA Medical S.A., Montrouge, France

[21] Appl. No.: 797,379

[22] Filed: Feb. 7, 1997

[30] Foreign Application Priority Data

Feb. 8, 1996 [FR] France ................ 96 01564

[51] Int. Cl.$^6$ ................ A61N 1/08
[52] U.S. Cl. ................ 607/59
[58] Field of Search ................ 128/920; 607/27, 607/30, 31, 59

[56] References Cited

U.S. PATENT DOCUMENTS

| 4,513,743 | 4/1985 | Van Arragon et al. | 128/419 |
| 4,712,179 | 12/1987 | Heimer | 364/417 |
| 5,036,869 | 8/1991 | Inahara | 128/903 |
| 5,321,618 | 6/1994 | Gessman | 364/413.06 |
| 5,456,691 | 10/1995 | Snell | 607/30 |
| 5,456,692 | 10/1995 | Smith, Jr. et al. | 607/31 |

FOREIGN PATENT DOCUMENTS

| 0 730 882 A2 | 11/1996 | European Pat. Off. | A61N 1/372 |
| 8602567 | 5/1986 | WIPO | 607/59 |
| WO 92/03776 | 3/1992 | WIPO | G06F 3/00 |

OTHER PUBLICATIONS

Zazula et al, "Computer-assisted exercise ECG analysis: real-time scheduling within MS-DOS on PCs" *Microprocessors and Microsystems*, vol. 18, No. 9, Nov. 1994 (pp. 523-535).

Dojat et al., "An Extendable Knowledge-Based system For The Control Of Mechanical Ventilation", *IEEE* Oct. 29, 1992, two pages.

Sukuvaara et al., "Object Oriented Implementation of an Architecture for Patient Monitoring", *IEEE Engineering in Medicine and Biology*, Dec. 1993 (pp. 69-81).

Westerteicher, "Introduction to the HP Component Monitoring System", *Hewlett Packard Journal*, vol. 42, No. 4, Oct. 1993, (pp. 6-10).

Herrera-Bendezu et al., "Integrated Cardiac Workstation for Image and Signal Processing" *Proceedings of the Annual International Conference of the IEEE Engineering in Medicine and Biology Society*, Oct. 1992, vol. 14 (pp. 2720-2721).

Snyder et al., "A Secure Communications and Status Reporting Protocol for Implanted Devices ", *Proceedings Sixth Annual IEEE Symposium on Computer Based Medical Systems*, Jun. 1993, (pp. 253-257)

*Primary Examiner*—William E. Kamm
*Attorney, Agent, or Firm*—Orrick, Herrington & Sutcliffe, LLP

[57] ABSTRACT

A system and methods for the automatic update of the software of an external programmer implant is that is used to program and configure an active implantable medical device implant and acquire data obtained by the implant. The programmer comprises software composed of an assembly of software objects. The implant comprises a memory containing parametric data for the functioning of the implant and an assembly of software objects necessary for the functioning of the programmer in connection with the aforementioned of parametric data. The programmer and the implant communicate bi-directionally. The automatic updating preferably occurs by the programmer reading of the memory of the implant, establishing a list of objects that are found in the implant with their respective versions, comparing the list to the objects (and their versions) that are in the programmer software, downloading from the implant of those objects which are not found in the programmer software and adding these objects to the programmer software; and/or downloading from the implant those objects in the programmer software whose version is prior to the version of the object found in the implant, and to replace the programmer software objects, with the more current version.

18 Claims, 2 Drawing Sheets

SYSTEMS, METHODS, AND APPARATUS FOR AUTOMATIC UPDATING OF A PROGRAMMER FOR AN ACTIVE IMPLANTABLE MEDICAL DEVICE

FIELD OF THE INVENTION

The present invention is directed to external programming machines that communicate with active implantable medical devices and exchange data therewith.

BACKGROUND OF THE INVENTION

The invention will be mainly described in the case of a cardiac pacemaker, but this is only one example of an implementation of the present invention, which is applicable in a far more general manner to a very great variety of "active implantable medical devices." Active implantable medical devices are defined, for example, by the Jun. 20, 1990 Directive 90/385/CCE of the European Community Council, to include, in addition to cardiac pacemakers, defibrillators and/or cardiovertors, diffusion/infusion pumps of medical substances, cochlear implants, implanted biological collectors, etc.

These devices (hereafter collectively designated "implants"), once put in place in a patient, that is, implanted, are programmed (and typically also reprogrammable to one extent or another) by an external programming device to perform the intended function in a desired manner. The external device is typically called a "programmer" and generally is a microcomputer equipped with a programming head placed in proximity with the site of the implant. The programmer can read, by way of electromagnetic transmission (wireless telemetry) through the programming head the data stored in the implant. For example, the programmer can read the parametric data, biological signals that have been recorded by the implant, events diagnosed by the implant, etc. The programmer typically also is able to send parametric data to the implant so as to re-program it, that is to say to modify some parameters of implant functioning, and may be able to send programming instructions to the implant to reconfigure its software. The term "parametric data" should be understood to mean and include the parameters used to program and/or control the functioning of the implant, which parameters may be predetermined at the time of construction of the implant or programmed/programmable values based on the intended use of the device, and also are referred to herein as "data".

The known programmers are specific to a given type of implant, or to a family of implants of the same manufacture. Consequently, each time a new implant is placed on the market, it is generally required to provide a corresponding update of the applicable programmers. In addition, even in the absence of placement on the market of a new implant, improvements are regularly obtained that can require an update of the programmer software.

These updates are particularly delicate. Indeed, for self-evident security reasons, all updates have to be released according to a very strict protocol: The protocol typically require a visit to the responsible health center or clinic where the programmer is maintained so that a qualified person can then change the program and recover the prior program. This visit is completed with a writing and signature of various certification documents, etc. These procedures are burdensome and costly. As a result, one typically avoids to follow them too often (for example, no update may be made in the case of a minor modification of the software).

In addition, the security procedures, as complete as they are, do not eliminate totally the risk of an absence of an appropriate update. For example, a programmer that could not be located by the manufacturer will not be updated. Nor do the procedures avoid the risks of operating during the update transition periods, and, especially, the less appropriate utilization of an obsolete version of the software. The reference to "obsolete" should be understood to mean simply a prior version that has been made obsolete by the update being implemented.

OBJECTS AND SUMMARY OF THE INVENTION

One of the objects of the present invention is, therefore, to remedy to these difficulties, by proposing a new concept of programmer whose software can be updated in an entirely automatic manner, without human intervention, thereby reducing, if not eliminating the burden, costs, and risks associated with current update procedures.

The invention relies on an implementation of the notion of an "object" in the software sense of the term, that is to say a structural element in the broadest sense of the term (data, constructors, destructors and methods), allowing the software to manage and to display data in a very structured manner.

In particular, the access to data is released in general only by methods appropriate to the object. This allows to protect the object data against exceeding a predetermined range and to render the software particularly reliable.

The concept of "heritage" or "inheritance" also facilitates the design of the software, with one object being able to inherit another object. This allows the one object to use directly the methods of the other object and simplify the structure of each with respect to updating by modification or addition of the one object, as will be explained. Examples of such software objects and their applications to the field of cardiac pacemakers will be described below.

In a general manner, one will be able to refer to the published literature on this subject of use of object programming, for example, the work of Max Bouché, "La démarche objet—Concepts et outils," AFNOR, 1994, (*The Step Object—Concepts and Tools, AFNOR*, 1994), as well as the documentation of typical "object oriented" programming languages such as C++.

Broadly, the invention is directed to (i) storing in the implant object oriented software, allowing it to define the display, the processing, and the programming of its data by an external programmer; (ii) comparing in the programmer a list of objects that the programmer contains to the list of objects that the implant contains; and (iii) downloading from the implant to the programmer objects in the implant that are missing in the programmer or more recent relative to the version of the object that is in the programmer, thereby to update the software of the programmer.

Proceeding in this manner, which is described in more detail hereafter, provides at least four major advantages as compared to the prior art updating procedures: security, economy, simplification of the programming, and standardization.

Security

All programmers are equipped with a basic minimum software, that is to say, objects allowing it to establish communication with an implant, and to manage connections between objects in the implant and objects in the programmer. Such a basic programmer will therefore able to read any implant and its objects, even if the implant has been developed well after the programmer and contains objects not previously in the programmer. Consequently, the operator of the programmer no longer will be unable to read and re-program the functions of a recent implant model in accordance with the present invention, if he has a compatible programmer, however old it may be. In addition, each parameter has its proper mode of management, defined by software in the implant, which controls the capture of these parameters by the programmer, and which is defined in a given object. Thus, the programmer will not capture false parameter values because they are no longer controlled by an object pre-existing in the programmer but rather by a object issued from the implant.

Economy

The expense of updating a programmer is considerably reduced and becomes required only for important equipment changes, (namely new generations of programmers, hardware changes telemetry heads, etc.). One also avoids all of the expense of the classic security procedures that go with the known update changes: manufacture of diskettes and manuals for the update, dispatching a qualified operator to each programmer site, signature of a register certifying the update, recovery of the old diskettes, etc.

Simplification of the Programming

The evolution and updating of the programmer software is performed automatically in a manner that is transparent to the user of the programmer.

Only very general functions will be needed to complete management of the basic objects, and the list of objects furnished will, at the end, be completed by the new or additional objects defined in each new implant.

Standardization

The flexibility of the implementation of the present invention allows the creation of a standard allowing all programmers to read compatibly any implant, regardless of its model or manufacturer. Each manufacturer will be able to define the graphic display aspect of its programmer, the possibilities of data management, supplementary calculations, etc. in a manner that will maintain a certain originality and product distinctiveness, but, with the basic objects being defined in an identical manner, the reading of a "foreign" implant now becomes perfectly possible.

One can thus envisage the realization of a universal programmer, which until now was excluded not only for reasons of cost and complexity, but also for security reasons (namely, the damages from unforeseen incompatibility risks).

One particular aspect of the invention is directed to a system comprising, on the one hand, an implant of the active implantable medical device type, and, on the other hand, an external programmer, in which:

The programmer has a software composed of an number of software objects;

the implant has a memory containing, on the one hand, parametric data concerning the functioning of the implant, and, on the other hand, a number of software objects necessary for the functioning of a programmer in connection with the aforementioned parametric data of the implant;

a bi-directional connection between the programmer and the implant to exchange information allowing particularly the selective transfer of all or part of the aforementioned parametric data and one or more of the aforementioned objects of the implant to the programmer; and the programmer has a programming capability to command the downloading from the implant of at least a part of the aforementioned objects contained in the implant memory and to add and/or to substitute these objects to the objects defined in the programmer software.

More preferably, the programmer downloads as much or as many of the implant objects as is necessary to become fully compatible with the implant. As a result the system is able to update the programmers. Preferably, the updating procedure occurs automatically when the programmer is placed in communication with the implant.

Advantageously, the programmer capability for updating operates to:

establish a list of objects that are found in the implant, more preferably a list which includes the version of the objects found;

compare the established list to the objects in the programmer software;

command the downloading from the implant of those objects absent in the programmer software and to add these objects to the programmer software; and/or command the downloading from the implant of those object for which the version present in the programmer software is prior to that found in the implant, and to replace therewith the objects in the software.

As a result, when an updated programmer is next in communication with a similar implant, the comparision of ojects in the implant to the programmer finds all of the current versions of the objects in the programmer, and no downloading is needed.

Other aspects of the invention are separately directed, as independent products, on the one hand, to the implant, and on the other hand, to the programmer, respectively implementing the appropriate one of the aforementioned characteristics.

DETAILED DESCRIPTION OF THE INVENTION

Figure 1:
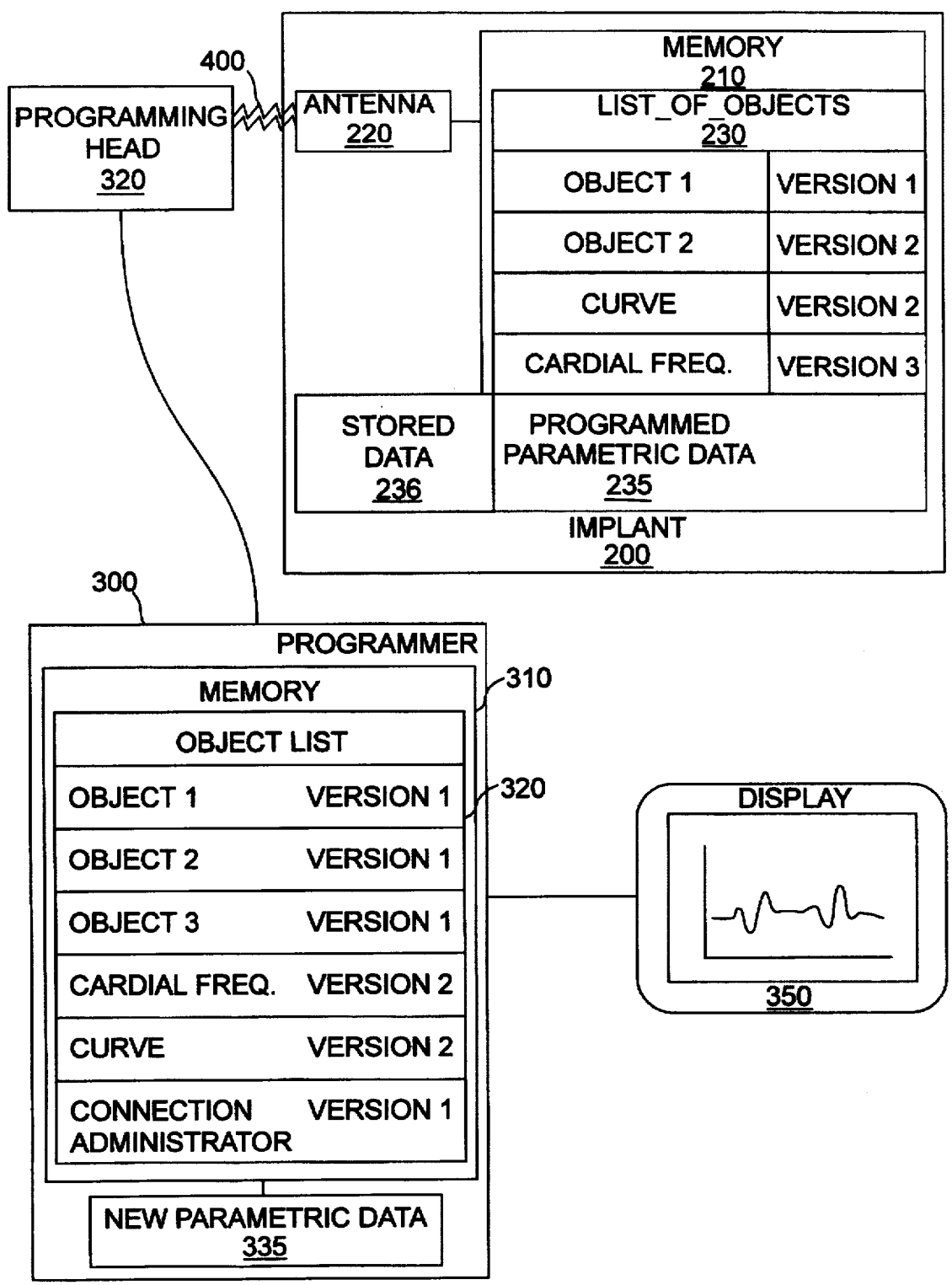
FIG. 1 is a block diagram of a system for reprogramming a programmer in accordance with the present invention.
Figure 2:
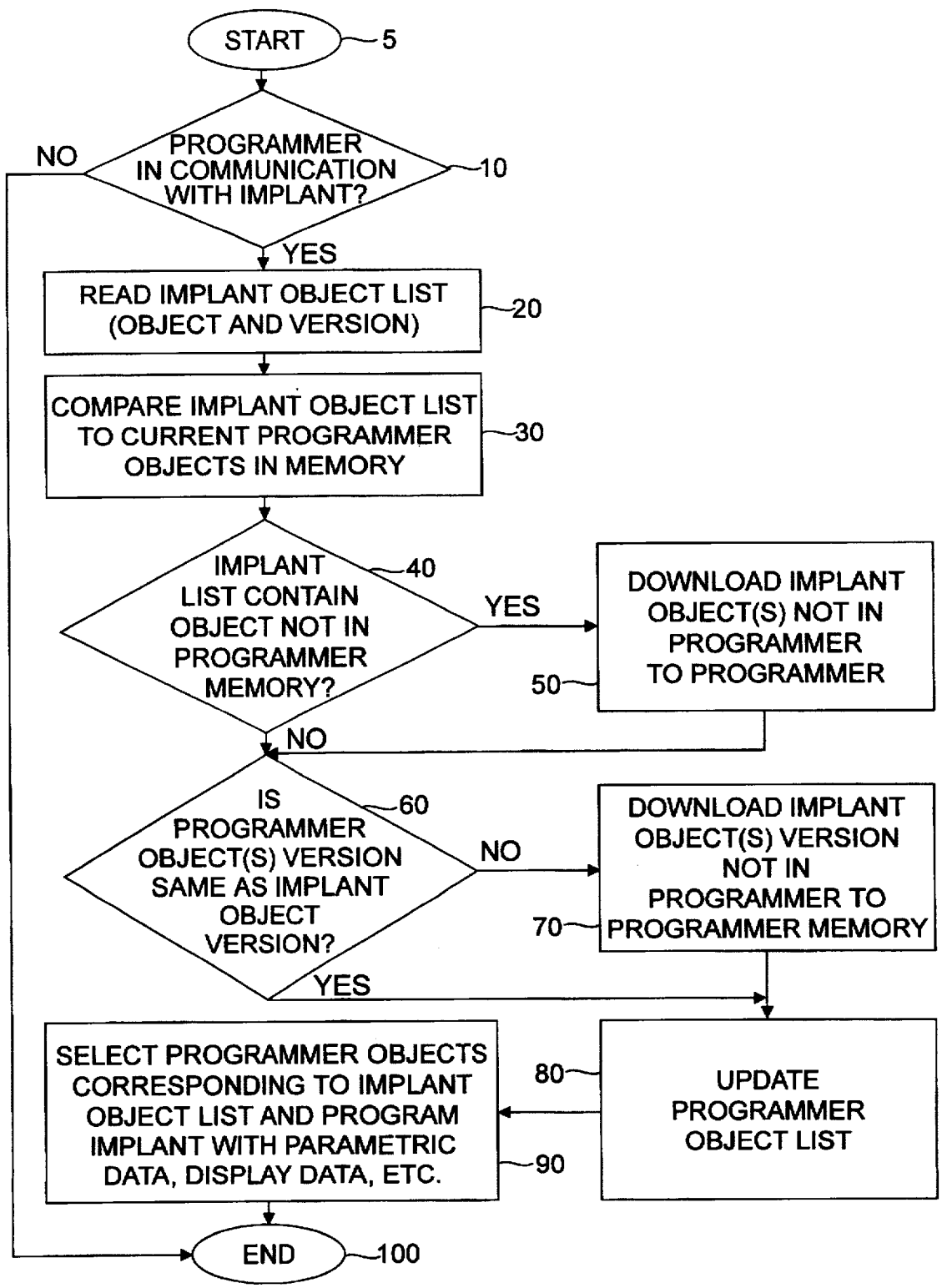
FIG. 2 is flow diagram for updating the programmer of the system of FIG. 1.

One is going now to describe an example of an implementation in accordance with a preferred embodiment of the invention with reference to FIGS. 1 and 2.

As previously indicated, the software of the programmer 300, as well as that of the implant 200, is organized in object oriented software "objects."

In the case of an implant 200 which is a cardiac pacemaker, one can represent by one object each element (parameter) of the pacemaker that is programmable or simply displayable on the screen 350 of a programmer or printable on a printer (not shown).

Thus, a curve giving the cardiac frequency as a function of time can be represented by a particular software object called "CARDIAC FREQUENCY," that inherits from a more general object, which one can call "CURVE," and comprises a sequence of data corresponding to a curve, with its format, its title, a method of display, a method of printing, etc. The term "format" refers to the scales in abscissa (X-axis) and ordinate (Y-axis).

The programmer 300 for its part has an object "CONNECTION ADMINISTRATOR" that can call data corresponding to the cardiac frequency stored in the pacemaker, by applying transfer data protocols, compression/decompression, etc. as necessary. The programmer 300 will then be able to display a window on the programmer screen 350 presenting the cardiac frequency data, with the help of the object CURVE, allowing all presently available display related functions: zooming, moving in the window, measuring the data displayed with the help of cursors, etc. These functions are understood to be performed in the conventional manner.

The concept of the invention is based on three fundamental hypotheses. First, the programmer software is "open," that is to say that it can be modified by receiving and incorporating new objects concerning data, the display of data, the processing of data, and the programming of the implant. These objects can come from the implant (according to the characteristic of the invention), from a diskette or from any other computer support in itself known (e.g., ROM change, a modem or file transfer), for example, by the preliminary loading of the CONNECTION ADMINISTRATOR object.

Second, the implant 200 stores all objects needed by it to define the programmer display, the data processing, and the programming of data contained in or acquired by the implant. It should be noted that the size of the objects in the implant software can be relatively reduced, to the extent that they inherit from other objects are already present in the programmer. For example, the programmer object CURVE generally defines the display and management of a curve, and therefore the implant software object CARDIAC FREQUENCY need only map the particular features of the data to be displayed to the object CURVE. The object CURVE then manages the actual processing and/or display.

Third, the versions of objects are dated (for example, by a version number and/or a date code) and any more recent version replaces a prior version in the programmer. Developments of objects is thus to be released by imposing an "upward" compatibility, that is to say, the more recent version remains compatible with all data exchanges relative to older versions.

In the beginning of the exchange of data between an implant 200 and a programmer 300 (step 10, FIG. 2), the programmer 230 systematically calls a block called List-Of-Objects that is a repertory of available objects in the implant (step 20, FIG. 2). This can be done automatically, preferably as soon as a valid communication link 400 is established (step 20, FIG. 2). This List-Of-Objects is maintained in the implant. Preferably, the List-Of-Objects also includes the version of each object in the implant. More preferably, the List-Of-Objects includes a table containing an object number and object name (and optionally a description).

The programmer 300 then compares the codes of these implant objects with the objects already known (e.g., an available list of objects in the programmer software 320, which is preferably dynamically managed and safeguarded in a configuration file) (step 30, FIG. 2). If one or more of these objects is unknown to the programmer, it calls the object CONNECTION ADMINISTRATOR and commences a procedure of downloading the unknown objects so as to complete its software and to adapt the programmer to the implant (steps 50 and 70, FIG. 2). The programmer configuration file is then updated (step 80, FIG. 2).

The procedure of downloading and updating automatically occurs for each unknown object (step 50, FIG. 2), by the programmer utilizing the CONNECTION ADMINISTRATOR object that inherits the object being downloaded. The CONNECTION ADMINISTRATOR sends a code, e.g., a number of the object, to the pacemaker and the pacemaker returns a block of corresponding information to the programmer.

A similar procedure is performed for objects that, although present in the software of the programmer, correspond to a version that is older than the one contained in the implant (step 70, FIG. 2).

After this updating phase, the programmer has all of the objects needed to be compatible with the implant, and can call all data (235 or 236) contained in the implant, to display the desired results, re-program the implant, etc. in the conventional manner (step 90, FIG. 2).

Thus, in the case of an implant having the object CARDIAC-FREQUENCY being read by a programmer not knowing that object, the programmer identifies the object in the List-Of-Objects provided by the pacemaker. The programmer then asks the implant to transfer the object, which it does, and the programmer adds it to its program. The call to the constructor of the object also allows to reserve a memory zone to receive later the curve of frequency, the selection of a display window and the initialization of various variables, associated with the object.

The code (or number) of the object CARDIAC-FREQUENCY then comes to be added to the dynamic list of available objects maintained in the software of the programmer.

When the programmer operator wants to display the curve, it calls on the programmer the corresponding window. The program then tests the presence of the curve in memory, and, if no curve exists, it commences a reading of the cardiac frequency data stored in the pacemaker. The curve is then displayed in a window having the classic display adjustment controls (gain, zoom, moving), measure (cursors) and possibly printing these various functions all being managed by the general object CURVE already present in the programmer.

One is going now to describe two detailed examples of pacemaker objects: an object NOMINAL FREQUENCY (programmed fixed value); and an object RESPIRATORY FREQUENCY (data which varies in the course of the time).

The description of objects can be released under any of several forms, which can be summarized as three cases: (1) machine code, (2) precompiled code and (3) metalanguage: The machine code or firmware is linked to the processor to allow a long term usage. The precompiled code (such as the old fashioned "P-code") is extremely effective, being able to describe all data and methods of the new objects. However, it remains large in size, and is thus less adapted to be used with implants having low memory capacity. The metalanguage specifies only the value of variables belonging to parent objects that are predetermined by the programmer. The volume of data is thereby extremely reduced as compared to the other cases.

Most of data of an implant can be contained in a description in the form of a metalanguage, but the recourse to a precompiled code should remain accessible for the integration with original objects.

In the examples described here, the chosen language is a metalanguage, which gives a reduced size of the objects and a total independence from the programming language. On the other hand, it can only make reference to the basic objects of the programmer, without being able to make them directly progress.

The limits are reached only when a completely new concept will not be able to be integrated by the programmer, with the result that the development of the basic objects has to be extremely well released to avoid the too frequent occurrence of this type of incident that would impose a traditional software update of programmers.

EXAMPLE 1
Object: NOMINAL FREQUENCY

The nominal frequency (also known as a base frequency), which is an essential parameter of all cardiac pacemakers, can be represented by an object described in the following manner:

1. object number: a unique code is associated with the object, for example, eight characters (two letters for the manufacturer, four letters for the object and two digits for the number of version). This allows to choose a code both unique and easily decipherable.
2. object ANCESTOR: a number for this object provides the code of the object ANCESTOR, that is the only object that already resides in this case in the programmer and allows the programmer to manage all processes of display, capture, printing and storing of a numerical value. This object inherits, of course, at a minimum, a more general object that is the CONNECTION ADMINISTRATOR. As it concerns a programming by predetermined steps, the values are coded in number of steps. This datum occupies five characters.

The next data provides the parameters of the object ANCESTOR:

(a) descriptive sentence (100 characters) accompanying the numerical value at the display (for example, twenty characters of text for a total of a hundred characters for twenty characters in five different languages).
(b) unit of measure (10 characters).
(c) values of the minimum, the maximum and the nominal value (16 characters): the limit is resident in the object ANCESTOR so as to prevent the capture of a numerical value out of the limits. These limits are updated by the maximum and the minimum and the nominal values replace the values previously present in the object during a call of a method of "placement to the nominal" which inherit all programmable objects. The step increment can be defined as a constant, logarithmic, or inverse function value in order to accommodate to the various cases existing in pacemakers.
(d) reference window (5 characters): Each datum to be displayed in one of the screens of the programmer, that can contain one or more windows. Each window is defined by the pacemaker with at least a title, a format (one column, two columns, etc.) and actions that one can execute (displacement, call to a momentary reading or continuous reading of the pacemaker, local menu, etc.)
(e) position in the reference window (5 characters): This provides column, height, etc., that can summarize in the form of a number to five digits: The first gives the column, the three following give an order of priority in relation to the others; the nucleus of screen-management places them from high to low by order of priority.

The totality of the data for this object occupy therefore 56 characters in monolingual mode and 136 characters in a multilingual mode.

EXAMPLE 2
Object: RESPIRATORY FREQUENCY

In the case of a pacemaker analyzing the respiratory frequency, the acquired data can be stored for periods of several hours, several days and even several months.

The object can be described in metalanguage in the following manner (Those terms already described are not repeated except as noted):

(1) number of object (8 characters)
(2) object ANCESTOR (5 characters) It concerns a curve generator in frequency as a function of time f(t) possessing a vertical scale and a horizontal scale, a format of data and a display mode (line, minimum—maximum, etc.), methods of scale change, display and printing. This object belongs to the objects residing in the programmer.

The next data give the parameters of the object ANCESTOR:

(a) descriptive sentence (20 characters for each language, or 100 characters in 5 language multilingual mode):
(b) unit of measure (10 characters).
(c) format of data (5 characters): continuation of numerical values (an integer) (8, 16, 24 or 32 bits), real, etc. This format is a resident object that inherits the object CONNECTION ADMINISTRATOR so as to render it capable to manage the transfer of data between the pacemaker and the programmer.
(d) time period separating each datum, (4 characters): period in milliseconds, coded by a four byte word allowing thus a dynamic range of time of between 1 ms and 1137 hours.
(e) vertical scale description (12 characters): low value, high value, step increment.
(f) reference window (5 characters): same as in the case of the nominal frequency.
(g) position in the reference window (5 characters): as for the nominal frequency, the display of the graph positions according to a certain order of priority; the number of columns and the number of displayed elements are taken into account by the window to grant to each the available maximum place: thus, a window with one column containing only one curve displays the former on all the available surface, a window with two columns and four curves displays each on a quarter of the total surface, area etc.

The totality of these data occupies therefore 74 characters in monolingual mode and 154 characters in a five language multilingual mode.

One can thus describe in the same general manner all of the necessary parameters for the functioning of the pacemaker.

In the case of a relatively complicated cardiac pacemaker, comprising for example 20 curves stored in memory and 50 programmable parameters, the total size of objects is thus, in multilingual mode, 50×136=6800 characters for parameters and 20×154=3080 characters for curves, for a total of 9880 characters. To this it is necessary to add the block List-of-Objects that will be transmitted to the programmer beforehand to perform the update, which is 70×8=540 bytes.

The total size reserved to the storing of objects in the pacemaker reaches, therefore, approximately 10 Kb in the case of the most complex (for example, a DDD rate responsive pacemaker of the most recent generation). Advantageously, these elements can be easily introduced in a ROM circuit of the pacemaker, without entailing overconsumption, so that this circuit is not activated.

One skilled in the art will appreciate that the present invention can be practiced by other than the described embodiments, which are presented for purposes of illustration and not of limitation.

I claim:

1. A system comprising, an active implantable medical device implant, and an external implant programmer, wherein:

the programmer further comprises a memory and a software stored in said memory having at least one software object;

the implant further comprises a memory containing parametric data associated with the functioning of the implant and at least one software object necessary for the functioning of the programmer in connection with said parametric data, wherein the programmer and the implant further comprise means to establish between them a bi-directional connection to exchange information, and means for allowing the selective transfer of at least a part of said at least one software object from the implant to the programmer; and the programmer further comprises means for commanding the downloading from the implant of at least a part of said at least one software object contained in the implant memory and storing in said programmer memory the downloaded part of said software object.

2. The system of the claim 1, in which the programmer further comprises:

means for reading a list of software objects in said implant;

means for establishing a list of software objects read;

means for comparing said established list and the software objects of the software stored in the programmer memory;

means for identifying as an absent software object an object in said established list and not in said programmer software, wherein the means for downloading downloads from the implant an identified absent object and adds the absent objects to the software in the programmer memory.

3. The system of claim 1 which wherein each implant software object has an associated version code corresponding to a date, and the programmer further comprises:

means for reading the memory of the implant and establishing a list of implant software objects and associated version codes;

means for comparing the established list to the programmer software objects and identifying a newer software object as an implant software object having a version code that is newer than the corresponding programmer software object; and means for downloading from the implant the identified newer software and replacing said downloaded newer software object for the corresponding programmer software object.

4. The system of claim 3 wherein the programmer further comprises means for comparing said established list to the programmer software objects and identifying an absent software object as an object in said established list and not in said programmer software, and wherein the downloading means further comprises means for adding said absent software object to the programmer software.

5. The system of claim 1 wherein each implant software object further comprises an identifying object, an identifying version and a block of program instructions and the programmer means for downloading downloads the block of program instructions for execution in connection with said parametric data, thereby updating said programmer for operation with said implant.

6. The system of claim 1 wherein said implant further comprises means for detecting a cardiac frequency of a patient and said at least one implant software object further comprises an object to display a nominal frequency for a cardiac pacemaker, wherein the programmer means for downloading downloads said display object and the programmer further comprises a display, and means for executing said downloaded display object to display the nominal cardiac frequency of said implant.

7. The system of claim 1 wherein said implant further comprises means for detecting a cardiac frequency of a patient over time and said at least one implant software object further comprises an object to display a cardiac frequency over a time measure, wherein the programmer means for downloading downloads said display object and the programmer further comprises a display, and means for executing said downloaded display object to display the cardiac frequency over time detected by said implant.

8. An active implantable medical device implant having a predetermined function comprising:

a memory, a software program in said memory, and parametric data for the functioning of the implant, means for establishing a bidirectional information exchange with an external programmer including an antenna and means responsive to an external command from an external programmer for downloading information in said implant memory to said external programmer;

wherein the software further comprises at least one software object for the functioning of a programmer in connection with programming the parametric data of said implant, said at least one object being downloadable to an external programmer.

9. The implant of claim 8 wherein each software object stored in said implant memory further comprises an associated version code corresponding to a date.

10. The implant of claim 8 wherein the software stored in said implant memory further comprises a list of each downloadable software object in said implant.

11. The implant of claim 10 wherein each software object stored in said implant memory further comprises an associated version code corresponding to a date, wherein said list further comprises said version code for each software object.

12. An external programmer for use with an active implantable medical device implant, comprising:

a software, having at least one software object;

bi-directional information exchange connection by selective transfer from the implant to the programmer, of a datum of the functioning of the implant and a software object necessary for the functioning of a programmer in connection with the aforementioned implant; and means for downloading from the implant of at least a part of said at least one software object and storing said downloaded software object as part of the programmer software.

13. The programmer of claim 12, in which the means for downloading further comprises means for reading the memory of the implant;

means for establishing a list of objects found in said implant memory with their respective version code;

means for comparing the established list to at least one of the objects of the programmer software and determining whether or not the at least one object is absent from the list and, if not absent, determining whether the at least one object is a version prior to the object version in said programmer memory, and means for commanding the downloading from the implant of the determined absent objects of the programmer software and to add these objects to the programmer software, and means for commanding the downloading from the implant of the determined objects present in programmer software but whose version is prior to the one found in the implant, and to replace these objects in the programmer software.

14. The programmer of claim 12, in which each software object further comprises at least an identifying object, an identifying version and a block of program instructions, wherein the means for downloading said at least a part of said at least one software object downloads and stores in said programmer memory said block of program instructions and said identifying versions for said block of program instructions.

15. A method for updating a programmer for an active medical device implant having a predetermined function and parametric data programmable by said programmer comprising:

a) providing a programmer with object oriented software and a list of objects in said programmer;

b) providing an implant with object oriented software, a plurality of objects, and a list of objects in said implant;

c) placing the programmer in communication with said implant; and automatically thereafter i) reading the list of objects in said implant memory;
ii) comparing the list of objects in said implant memory to said list of objects in said programmer; and
iii) updating the objects in said programmer and said list of objects in said programmer.

16. The method of claim 15 wherein step (c)(ii) further comprises identifying each object in said implant list that is not in said programmer list, and step (c)(iii) further comprises down-loading each said identified object into said programmer and modifying the list of objects in said programmer.

17. The method of claim 16 wherein:

step (a) further comprises providing each programmer object with a version code;

step (b) further comprises providing each implant object with a version code;

step (c) (i) further comprises reading the version code of each implant object;

step (c) (ii) further comprises comparing the version code of each object on the list of implant objects read to the version code of the objects on the list of programmer objects and determining, for each implant object, if its version code is newer than a corresponding programmer object version code; and step (c) (iii) further comprises downloading each determined newer implant object and its version code and replacing said corresponding programmer object and version code with said downloaded object and version code.

18. The method of claim 17 wherein in step (c) (ii) further comprises identifing each object in said implant list that is not in said programmer list, and step (c) (iii) further comprises downloading each said identified object into said programmer and modifying the list of objects in said programmer.

* * * * *